United States Patent
Maack et al.

(10) Patent No.: US 8,033,725 B2
(45) Date of Patent: Oct. 11, 2011

(54) X-RAY IMAGE APPARATUS AND DEVICE FOR AND METHOD OF CALIBRATING AN X-RAY IMAGE APPARATUS

(75) Inventors: Hanns-Ingo Maack, Norderstedt (DE); Christoph Kurze, Kamenz (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 72 days.

(21) Appl. No.: 12/302,899

(22) PCT Filed: May 22, 2007

(86) PCT No.: PCT/IB2007/051925
§ 371 (c)(1),
(2), (4) Date: Dec. 1, 2008

(87) PCT Pub. No.: WO2007/141689
PCT Pub. Date: Dec. 13, 2007

(65) Prior Publication Data
US 2009/0245473 A1    Oct. 1, 2009

(30) Foreign Application Priority Data
Jun. 2, 2006 (EP) .................................. 06114938

(51) Int. Cl.
*G01D 18/00* (2006.01)
(52) U.S. Cl. .................... 378/207; 382/131; 382/132

(58) Field of Classification Search .................... 378/19, 378/98.8, 196, 197, 189, 190, 207; 250/370.09; 382/131, 132
See application file for complete search history.

(56) References Cited

U.S. PATENT DOCUMENTS 5,745,542 A * 4/1998 Gordon et al. .................... 378/4
6,041,097 A * 3/2000 Roos et al. ....................... 378/62
(Continued)

FOREIGN PATENT DOCUMENTS
EP    0973047 A2    1/2000
(Continued)

OTHER PUBLICATIONS

Anthony Brinton Wolbarst, Physics of Radiology (Connecticut: Appleton & Lange, 1993), p. 102.*

(Continued)

*Primary Examiner* — Allen C. Ho (57) ABSTRACT

A calibration device (140) for calibrating an X-ray image apparatus includes a receiving unit (200) for receiving an image captured by a detection unit (108) of the X-ray image apparatus (100) under reference conditions, an analyzing unit (201) for analyzing the captured image to derive gain correction information, and a calibration unit (202) for providing calibrating information for calibrating the X-ray image apparatus (100) based on the derived gain correction information disregarding gain correction of a heel effect.

19 Claims, 4 Drawing Sheets

U.S. PATENT DOCUMENTS

| | | | |
|---|---|---|---|
| 6,428,206 B1 * | 8/2002 | Watanabe | 378/197 |
| 6,639,966 B2 * | 10/2003 | Lautenschlager et al. | 378/15 |
| 6,879,660 B2 * | 4/2005 | Dhawale et al. | 378/98.8 |
| 6,968,042 B2 * | 11/2005 | Toth et al. | 378/156 |
| 7,020,243 B2 * | 3/2006 | Hsieh | 378/62 |
| 7,056,018 B2 * | 6/2006 | Stierstorfer et al. | 378/207 |
| 7,110,588 B2 * | 9/2006 | Dewaele et al. | 382/132 |
| 7,224,771 B2 * | 5/2007 | Levene et al. | 378/144 |
| 7,315,640 B1 * | 1/2008 | Brady et al. | 382/132 |
| 7,340,030 B2 * | 3/2008 | Altman et al. | 378/19 |
| 7,397,904 B2 * | 7/2008 | Virshup et al. | 378/156 |
| 7,430,282 B2 * | 9/2008 | Mori et al. | 378/159 |
| 7,480,363 B2 * | 1/2009 | Lasiuk et al. | 378/54 |
| 7,538,317 B2 * | 5/2009 | Cresens et al. | 250/252.1 |
| 7,676,073 B2 * | 3/2010 | Hamill et al. | 382/128 |
| 7,724,935 B2 * | 5/2010 | Van Stevendaal et al. | 382/132 |
| 2004/0120468 A1 | 6/2004 | Dhawale et al. | |

FOREIGN PATENT DOCUMENTS

| | | |
|---|---|---|
| EP | 0982683 A2 | 3/2000 |
| WO | 9923670 A1 | 5/1999 |
| WO | 0126132 A1 | 4/2001 |
| WO | 2005006257 A2 | 1/2005 |

OTHER PUBLICATIONS

Jarry Geneviève et al: "Characterization of scattered radiation in kV CBCT images using Monte Carlo simulations" Medical Physics, AIP, Melville, NY, US, vol. 33, No. 11, Oct. 24, 2006, pp. 4320-4329, XP012091941 ISSN: 0094-2405.

* cited by examiner

X-RAY IMAGE APPARATUS AND DEVICE FOR AND METHOD OF CALIBRATING AN X-RAY IMAGE APPARATUS

FIELD OF THE INVENTION

The invention relates to a calibration device for calibrating an X-ray image apparatus.

Furthermore, the invention relates to an X-ray image apparatus.

Moreover, the invention relates to a method of calibrating an X-ray image apparatus.

Beyond this, the invention relates to a program element.

Furthermore, the invention relates to a computer-readable medium.

BACKGROUND OF THE INVENTION

X-ray imaging is important in many technical fields including medical applications, baggage inspection, or material science.

Over the past several years, X-ray baggage inspections have evolved from simple X-ray imaging systems that were completely dependent on an interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

It may be advantageous to calibrate an X-ray image apparatus to improve accuracy.

WO 2005/006257 A2 discloses an imaging system comprising artifact reduction means arranged to correct for a ring-shaped artifact in the three-dimensional reconstructed volume. The artifact reduction means comprises a first stage correction means arranged to eliminate the structured noise of the output screen of the image intensifier of an X-ray imaging apparatus using a first corrective image. The first corrective image may be pre-calculated and stored in a suitable memory unit of a computer. A raw image of the patient is first processed with the first corrective image. The thus obtained gain-corrected image is forwarded to an image deformation correction means, where a suitable unwarping function is being pre-stored. The resulting gain-corrected unwarped images are then made available to the second stage gain correction means, where a second corrective image is applied to the images resulting in a final set of images with a substantially reduced ring-shaped artifact. The final set of images is made available to the image reconstruction means arranged for further processing of the final set of images, the result thereof being visualized on a computer monitor for inspection purposes.

However, the system of WO 2005/00657 A2 may suffer from insufficient gain correction capabilities under undesired circumstances.

OBJECT AND SUMMARY OF THE INVENTION

It is an object of the invention to enable a proper calibration for an X-ray apparatus.

In order to achieve the object defined above, a calibration device for calibrating an X-ray image apparatus, an X-ray image apparatus, a method of calibrating an X-ray image apparatus, a program element, and a computer-readable medium according to the independent claims are provided.

According to an exemplary embodiment of the invention, a calibration device for calibrating an X-ray image apparatus is provided, the device comprising a receiving unit for receiving an image captured by a detection unit of the X-ray image apparatus under reference conditions, an analyzing unit for analyzing the captured image to derive gain correction information, and a calibration unit for providing calibrating information for calibrating the X-ray image apparatus based on the derived gain correction information disregarding gain correction of a heel effect.

According to another exemplary embodiment of the invention, an X-ray image apparatus for examination of an object of interest is provided, the X-ray image apparatus comprising an X-ray source for emitting an X-ray beam to the object of interest, a detection unit for detecting the X-ray beam having propagated through the object of interest, and a determining unit for determining structural information concerning the object of interest under consideration of calibrating information provided by a calibration device having the above mentioned features.

According to still another exemplary embodiment of the invention, a method of calibrating an X-ray image apparatus is provided, the method comprising receiving an image captured by a detection unit of the X-ray image apparatus under reference conditions, analyzing the captured image to derive gain correction information, and providing calibrating information for calibrating the X-ray image apparatus based on the derived gain correction information disregarding gain correction of a heel effect.

According to yet another exemplary embodiment of the invention, a computer-readable medium is provided, in which a computer program of calibrating an X-ray image apparatus is stored which, when being executed by a processor, is adapted to control or carry out a method having the above mentioned features.

According to still another exemplary embodiment of the invention, a program element of calibrating an X-ray image apparatus is provided, which program element, when being executed by a processor, is adapted to control or carry out a method having the above mentioned features.

Data processing for calibration purposes which may be performed according to embodiments of the invention can be realized by a computer program, that is by software, or by using one or more special electronic optimization circuits, that is in hardware, or in hybrid form, that is by means of software components and hardware components.

According to an exemplary embodiment, an X-ray image apparatus may be calibrated in an efficient manner. For this purpose, a gain correction scheme may be applied which may be less prone to failure than conventional gain correction schemes. Particularly, when an essentially two-dimensional detector is turned, rotated or moved, artefacts due to a heel effect compensation may be efficiently suppressed.

For this purpose, it is possible to receive an image under reference conditions, that is to say without an object of interest in the X-ray beam path, with a constant exposure to X-rays over the detector area. In other words, the reference measurement may be free of an object between X-ray source and detector, or a "neutral" object (for instance made of a homogenous material) may be positioned between X-ray source and detector. By taking this measure, it may be ensured that essentially no intensity differences occur over the active detector area due to an object of interest in the X-ray beam path.

Such a reference image may then be analyzed by an analyzing unit with regard to different gain correction contributions, for instance determining separate components of detector gain characteristics, rotational symmetric components, and a one-dimensional gradient originating from the so-called heel effect. The analysis may include performing a computer fit to derive fit parameters indicative of the captured reference image in view of a theoretical model for the different contributions to artefacts.

A calibration unit may perform the actual calibration based on one or more components of this analysis, but may selectively disregard heel effect contributions. By taking this measure, it may happen that a slight intensity profile remains due to the non-compensated heel effect. However, in case of rotation of the detector, omitting the heel effect compensation may improve the accuracy of the gain correction significantly.

The term "heel effect" (or anode heel effect) may have its origin in that an X-ray beams intensity may be not uniform throughout its entirety. For instance, as X-radiation is emitted from a target area in a conical shape, it may happen that the intensity in the direction of the anode is lower than the intensity in the direction of the cathode. The fact that the intensities vary in such a manner may cause visible differences in the density produced on the detected spectra. This phenomenon may be called the heel effect.

Exemplary embodiments of the invention may allow for an improved gain correction for rotated X-ray detectors, by taking into account the heel effect in a modified manner. Particularly, such a scheme may serve for flat panel CT gain correction comprising several correction components.

In the field of flat panel X-ray detectors it is common to perform a "gain correction". For this purpose, a homogeneously exposed image $G_{all}$ may be taken and stored as a reference. All later X-ray images may be divided by this gain reference. This concept may be appropriate for square detectors, which are fixed in systems. With this correction, not only the detector gain may be corrected but also simultaneously the influence from the geometrical factors.

Such a scheme may be advantageous as long as the geometrical conditions do not change too much. Detectors having a rectangular shape (with sides having different lengths) can usually be rotated with respect to the system geometry, which may lead to a problem with a regular gain correction. Exemplary embodiments of the invention are related to a procedure to overcome or suppress such problems.

A detailed analysis of the $G_{all}$ shows three components:

$G_{detector}$: detector gain characteristics from the detector hardware. Such a detector gain characteristics may result in a stripe-like pattern (see FIG. 3).

$G_{radius}$: rotational symmetric component of gain, depending on SID (source image distance) and radius from image center. Such a component may provide an $r^2$ term, that is to say a radial distribution of the intensity along a rectangular or square detector element, wherein r may be a distance from a detector center (see FIG. 3).

$G_{heel}$: one-dimensional gradient originating from the "heel effect" of the X-ray tube. Such a contribution may result in intensity differences along one axis of the detector element, while being essentially constant along the second dimension (see FIG. 3).

The term "$G_{all}$" may particularly denote a homogeneously exposed image for gain calibration (average). $G_{all}$ is a full resolution matrix with one figure per pixel.

$G_{radius}$ may denote a rotational symmetric component of gain, depending on SID (source image distance) and radius from image centre. $G_{radius}$ may be a polynom depending on x and y.

$G_{heel}$ may denote a linear gradient from the "heel effect" of the X-ray tube. $G_{heel}$ may be a polynom depending on y only.

The term "$G_{detector}$" may denote a detector gain characteristic from the detector hardware. $G_{detector}$ may be a full resolution matrix that can be calculated from $G_{all}/(G_{radius} \cdot G_{heel})$.

$G_{all}$ may be determined according to the following equation:

$$G_{all} = G_{detector} \cdot G_{radius} * G_{heel}$$

Conventionally, a gain correction $G_{all}$ for a rotated detector may be performed using such an equation.

The heel effect may lead to a significant image artifact when an original gain reference correction is based on images from a detector that has been rotated by 90°. The "new" heel effect may be out of consideration and is not at all corrected by the gain correction. In opposite, the inverse "old" heel effect is introduced as pattern from bottom to top which leads to a diagonal inhomogeneity.

According to an exemplary embodiment of the invention, no heel effect correction is carried out intentionally, that is to say detector gain characteristic correction and/or rotational symmetric gain correction only is performed.

The terms $G_{radius}$ and $G_{heel}$ can be derived from a (theoretical) fit to the (experimental) $G_{all}$ data:

$$G_{radius}: r(x,y) = r_1(x^2+y^2) + r_2\sqrt{x^2+y^2} + r_3 \text{ with coefficients } r_1, r_2, r_3$$

$$G_{heel}: h(y) = h_1 y^5 + h_2 y^4 + h_3 y^3 + h_4 y^2 + h_5 y + h_6.$$

The original heel effect may be re-introduced after the gain correction:

$$\text{Gain correction factor} = \frac{1}{G_{all}} \cdot \frac{G_{heel}}{1}$$
$$= \frac{1}{G_{detector} \otimes G_{radius}}$$

Figure 5:
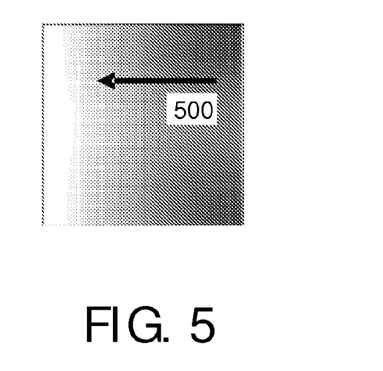

An example image of the true heel effect is shown in FIG. 5, illustrating only the original heel effect from the right to the left. The vertical one is no more present. In this example, the radius-dependent term is still corrected. There is another option to skip this correction as well, with the result that only the detector determined term will be corrected. This would lead to a similar correction concept as for CR image plates, which show the unmodified X-ray profile as well.

Exemplary embodiments of the invention may have the advantage that there is essentially no dependency on the spatial orientation of the detector in respect to the calibration. Any orientation would perform alike, the orientation does not even has to be known (as, for instance, in the case of a wireless portable X-ray detector).

Furthermore, the corrected images may show the "true X-ray distribution", the local signal will be correlated to the local X-ray intensity.

Beyond this, the images from the flat panel detectors may look more similar to images from CR plates.

Next, further exemplary embodiments of the invention will be explained. In the following, further exemplary embodiments of the calibration device will be explained. However, these embodiments also apply for the X-ray image apparatus, the method of calibrating an X-ray image apparatus, the program element and the computer-readable medium.

The reference conditions may comprise capturing the image under essentially homogenous X-ray exposure conditions. In other words, no significantly inhomogeneous object which may cause a dark light pattern on the detector area may be provided between the X-ray radiation source and the detector. In contrast to this, no object or a homogenous reference object which should have no significant influence on the exposure of the radiation to the detector may be positioned between the X-ray source and the detector. This may allow to detect a reference pattern which allows an analysis of the gain correction contributions.

The analyzing unit may be adapted to derive the gain correction information under consideration of at least one of the group consisting of gain correction due to a hardware characteristic of the detection unit ($G_{detector}$), gain correction due to rotational symmetric artefacts ($G_{radius}$), and gain correction due to the heel effect ($G_{heel}$). Advantageously, the analyzing unit may take into account all three contributions, particularly no further contribution. In other words, it may be possible to separate contributions of only these three disturbing effects by the analyzing unit.

Furthermore, the analyzing unit may be adapted to derive the gain correction information by fitting a theoretical model to the captured image. Such a computer fit may be based on a least squares fit algorithm to minimize the least square deviations between the measured spectrum and the fit spectrum. By taking this measure, parameters of the different contributions to the gain correction in the context of a theoretical model may be extracted.

Moreover, the calibration unit may be adapted for providing the calibrating information based on the derived gain correction information under consideration of at least one of the group consisting of gain correction due to a hardware characteristic of the detection unit ($G_{detector}$), and gain correction due to rotational symmetric artefacts ($G_{radius}$). However, the calibration unit may disregard any contributions originating from the heel effect ($G_{heel}$) so as to suppress artefacts which may result from a motion (for instance rotation) of the detector. According to one exemplary embodiment, the influences of the hardware characteristics of the detection unit and the gain correction due to rotational symmetric artefacts may be taken into account for calibration. According to another exemplary embodiment, only the gain correction due to a hardware characteristics of the detection unit may be considered, neglecting not only the heel effect but also the gain correction due to rotational symmetric artefacts.

The calibration unit may be adapted for providing the calibration information by calculating a gain correction factor by multiplying a gain correction factor indicative of gain correction due to a hardware characteristics of the detection unit with a gain correction factor indicative of rotational symmetric artefacts. By taking this measure, these two contributions may be considered, however the heel effect may be selectively disregarded.

The calibration unit may be adapted for providing the calibration information by calculating a gain correction factor of gain correction due to a hardware characteristic of the detection unit. According to this embodiment, only the hardware characteristic of the detection unit is used for gain correction, which allows a relatively good gain correction with low computational burden.

In the following, further exemplary embodiments of the X-ray image apparatus will be explained. However, these embodiments also apply to the calibration device, to the calibration method, to the program element and to the computer-readable medium.

The X-ray image apparatus may comprise a rotatable gantry, wherein the electromagnetic radiation source (for instance an X-ray tube) and the detection unit (for instance a scintillation detector with a diode array, or a CCD camera) may be arranged on the gantry. Therefore, the gantry may rotate around an object of interest (for instance a patient or a baggage item), and optionally a translation motion of the object with respect to the rotating gantry is possible (depending on whether a helical scan or a circular scan is desired). It is also possible to rotate the detection unit being installed on the rotatable gantry, that is to say around a rotation axis which may differ from the rotation axis of the rotatable gantry. Such a movable detector configuration may increase the flexibility in using such an X-ray image apparatus. With the gain correction scheme according to an exemplary embodiment of the invention, such a rotation of the detection unit with respect to the gantry is enabled, since such a rotation does not, in contrast to conventional systems, introduce a further artifact in this spectrum.

The X-ray image apparatus may be adapted as a computer tomography apparatus. A computer tomography apparatus may be denoted as an apparatus using digital processing to generate a three-dimensional image of the internals of an object from a series of two-dimensional X-ray images taken around a single axis of rotation. The reconstruction of CT images can be done by applying appropriate algorithms. For instance, such a CT apparatus may be a CSCT apparatus ("coherent scatter computer tomography").

The X-ray image apparatus may be adapted as a baggage inspection apparatus, a medical application apparatus, a material testing apparatus, and a material science analysis apparatus. However, all other purposes are possible in the context of the invention.

The detection unit may be movable relative to the electromagnetic radiation source. In other words, in addition or alternatively to the rotatable configuration of the detection unit with respect to the gantry, the latter may also be movable with respect to the electromagnetic radiation source (for instance using a translational and/or rotational motion). The elimination of the heel effect with regard to calibration in accordance with exemplary embodiments of the invention may allow to suppress artefacts which may conventionally originate from such a motion.

The detection unit may be rectangular and non-square. Although square detection units are possible, the combination of movable detection units and rectangular and non-square detection units may be particularly advantageous, since it may increase the flexibility of the system.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

The illustration in the drawing is schematically. In different drawings, similar or identical elements are provided with the same reference signs.

In the following, referring to FIG. 1, a computer tomography apparatus 100 according to an exemplary embodiment of the invention will be described.

Figure 1:
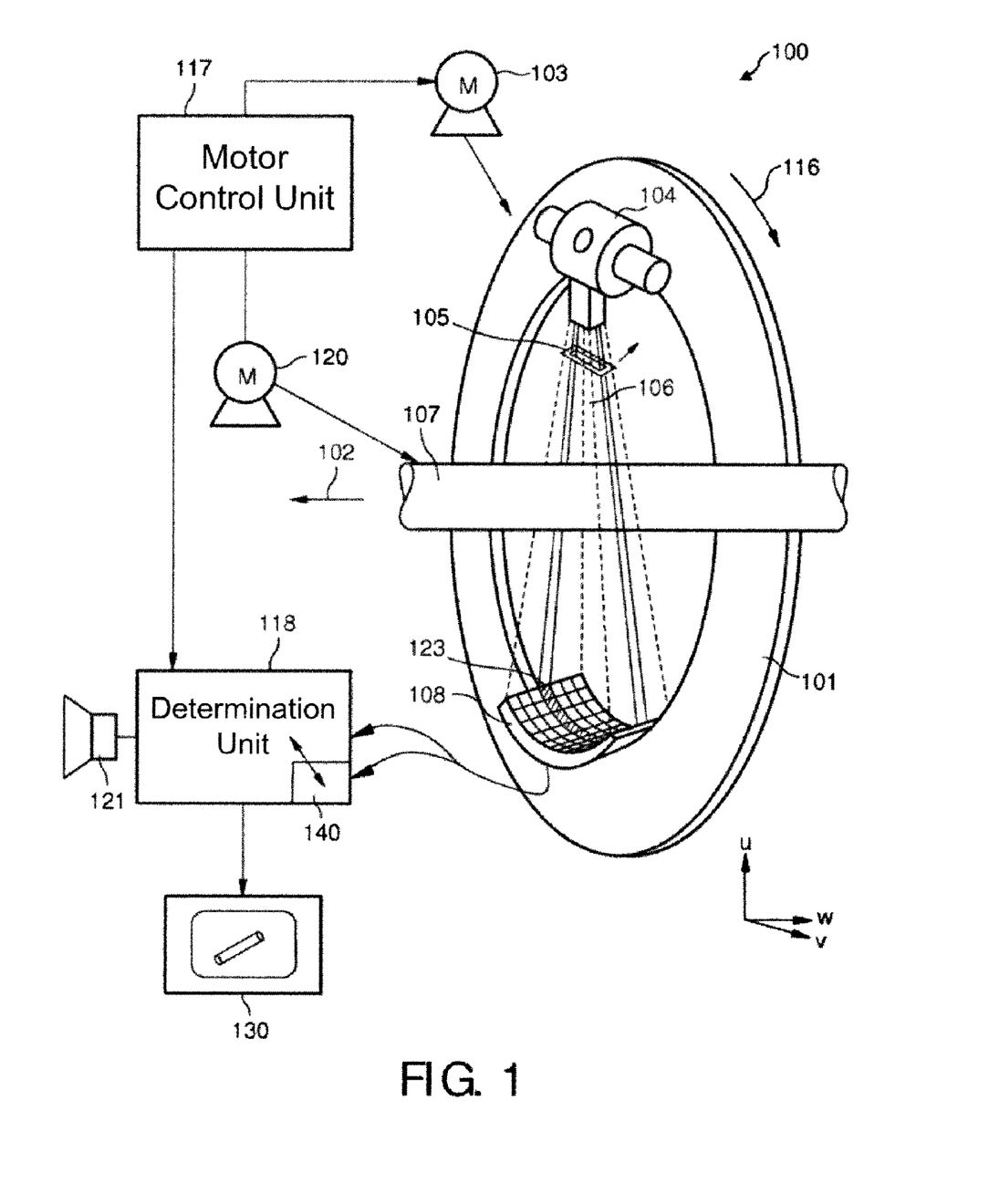
FIG. 1 shows a computer tomography apparatus according to an exemplary embodiment of the invention.

The computer tomography apparatus 100 depicted in FIG. 1 is a fan-beam CT scanner. The scanner depicted in FIG. 1 comprises a gantry 101, which is rotatable around a rotational axis 102. The gantry 101 is driven by a motor 103. Reference numeral 104 designates a source of radiation such as an X-ray source, which, according to an aspect of the present invention, may emit a polychromatic radiation or an essentially monochromatic radiation.

Reference numeral 105 designates an aperture system which forms the radiation beam emitted from the radiation source 104 to a fan-shaped radiation beam 106. The fan-beam 106 is directed such that it penetrates an object of interest 107 arranged in the center of the gantry 101, i.e. in an examination region of the scanner 100, and impinges onto a detector 108. As may be taken from FIG. 1, the detector 108 is arranged on the gantry 101 opposite to the source of radiation 104, such that the surface of the detector 108 is covered by the fan-beam 106. The detector 108 depicted in FIG. 1 comprises a plurality of detector elements 123 each capable of detecting, in an energy-resolving manner, X-rays which have been transmitted through the object of interest 107.

During a scan of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 is an item of baggage which is disposed on a conveyor belt (not shown). During the scan of the object of interest 107, while the gantry 101 rotates around the item of baggage 107, the conveyor belt displaces the object of interest 107 along a direction parallel to the rotational axis 102 of the gantry 101. By this, the object of interest 107 is scanned along a helical scan path. The conveyor belt may also be stopped during the scans to thereby measure signal slices. Instead of providing a conveyor belt, for example in medical applications where the object of interest 107 is a patient, a moveable table may be used. However, it should be noted that in all of the described cases it is also possible to perform a circular scan, where there is no displacement in a direction parallel to the rotational axis 102, but only the rotation of the gantry 101 around the rotational axis 102.

As shown in FIG. 1, the invention can be realized by a fan-beam configuration. In order to generate a primary fan-beam, the aperture system 105 is configured as a slit collimator.

The detector 108 is connected to a determination unit 118. The determination unit 118 receives the detection result, i.e. the read-outs from the detector elements 123 of the detector 108 and determines a scanning result on the basis of these read-outs. Furthermore, the determination unit 118 communicates with a motor control unit 117 in order to coordinate the movement of the gantry 101 with motors 103 and 120 with the conveyor belt.

The determination unit 118 may be adapted for reconstructing an image from read-outs of the detector 108 using a tomographic reconstruction. A reconstructed image generated by the calculation unit 118 may be output by a display unit 130.

The determination unit 118 may be realized by a data processor to process read-outs from the detector elements 123 of the detector 108.

Furthermore, as may be taken from FIG. 1, the determination unit 118 may be connected to a loudspeaker 121, for example to automatically output an alarm in case of the detection of suspicious material in the item of baggage 107.

As can further be taken from FIG. 1, a calibration device 140 is provided for calibrating the X-ray image apparatus 100.

The calibration device 140 is coupled for data communication with the determining unit 118 and may provide calibration information to the determining unit 118. The determining unit 118, determining a three-dimensional structure of the object of interest 107, may then take into account the calibration information provided by the calibration device 140 so as to improve the quality or accuracy in determining the image.

Figure 2:
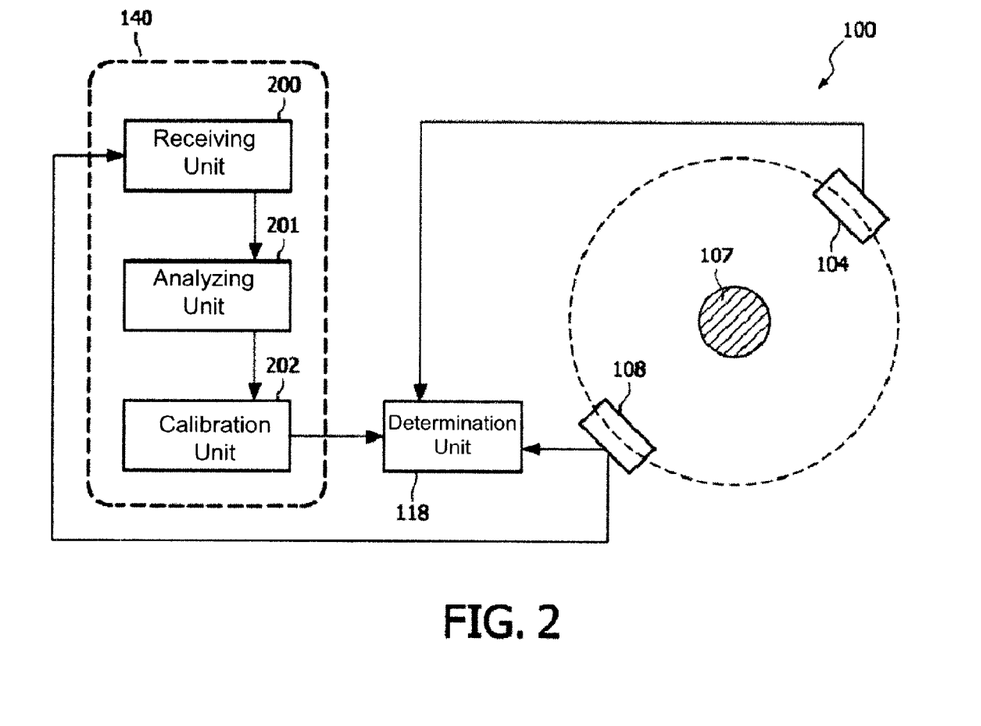
FIG. 2 shows a computer tomography apparatus with details of a calibration device according to an exemplary embodiment of the invention.

The functionality of the calibration device 140 will be explained in more detail referring to FIG. 2, showing a schematic view of the X-ray apparatus 100.

The calibration device 140 for calibrating the X-ray image apparatus 100 comprises a receiving unit 200 for receiving an image captured by the detection unit 108 of the X-ray image apparatus 100 under reference conditions. The reference conditions comprise capturing the image under essentially homogeneous X-ray exposure conditions. In other words, such a reference image is captured without the object of interest 107 being located between the X-ray tube 104 and the detector 108 to capture a reference image which comprises "only" disturbing components like artefacts.

This image data may be pre-processed by the receiving unit 200 to bring it in a format which is interpretable by an analyzing unit 201 for analyzing the captured image to derive gain construction information. The analyzing unit 201 analyzes this reference image and extracts from this image contributions of different gain correction origins, particularly a gain correction contribution due to a hardware characteristic of the detection unit 108 ($G_{detector}$), a gain correction contribution due to rotational symmetric artefacts ($G_{radius}$), and a gain correction due to the heel effect ($G_{heel}$). The analyzing unit 201 may fit a theoretical model for each of these contributions to the captured reference image and may derive fitting parameters, for instance applying a least squares fit (like a Marquardt fit).

The extracted components of the gain corrections may be supplied from the analyzing unit 201 to a calibration unit 202 for generating calibration information for calibrating the X-ray image apparatus 100 based on the derived gain correction information disregarding gain correction of the heel effect. In other words, a gain correction factor calculated by the calibration unit 202 may include only components of $G_{detector}$ and/or $G_{radius}$, but may not consider $G_{heel}$. By taking this measure, the introduction of further artefacts which may originate from a rotation of the detector 108 for instance in a plane perpendicular to the paper plane of FIG. 2 may be improved.

Resulting gain calibration information may then be supplied from the calibrating unit 202 to the determining unit 118 which can be taken into account by the determining unit 118 for determining a (true) image of the object of interest 107 with high accuracy. Such an X-ray image captured with the object 107 in the beam path between the X-ray tube 104 and the detector 108 may be divided by the gain reference estimated by the calibration unit 202.

In the following, a calibration scheme according to an exemplary embodiment of the invention will be explained in more detail.

Detectors in systems may be corrected conventionally using the unmodified reference image $G_{all}$. An X-ray image with the same conditions as the reference may be totally flat, meaning the local signal values are the same everywhere. Some artefacts with source image distance (SID) variations are conventionally known and accepted. Tube voltages below or above the value from the calibration lead to over-compensation or under-compensation of the heel effect.

However, as will be explained referring to the image plate 400 shown in FIG. 4, a problem with a rotated detector may occur with the conventional correction scheme.

The heel effect may lead to significant image artefacts when the original gain reference $G_{all}$ is applied to images from a detector that has been rotated by 90°.

Figure 4:
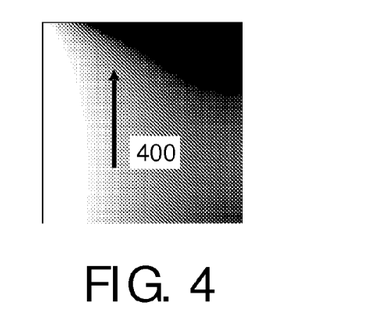

The "new" heel effect from the right to the left in FIG. 4 is not all corrected by the gain correction, in opposite, the inverse "old" heel effect is inversely introduced as a pattern from bottom to top which leads to diagonal inhomogeneity of the corrected image (SID=110 cm).

$$\text{Gain correction factor} = \frac{1}{G_{all}}$$

This explanation referring to FIG. 4 shows that, conventionally, artefacts may be introduced due to the way of including the gain effect into the correction procedure.

Individual calibrations for portrait and landscape image orientations are an option for systems. The system could know which orientation the detector has and select the proper gain reference. However, this may be inappropriate for a portable detector in free exposure mode.

According to an exemplary embodiment of the invention, a detailed analysis of the regular gain reference image $G_{all}$ shows the three above-mentioned components $G_{detector}$, $G_{radius}$, and $G_{heel}$. The following equation holds:

$$G_{all} = G_{detector} \cdot G_{radius} \cdot G_{heel}$$

Figure 3:
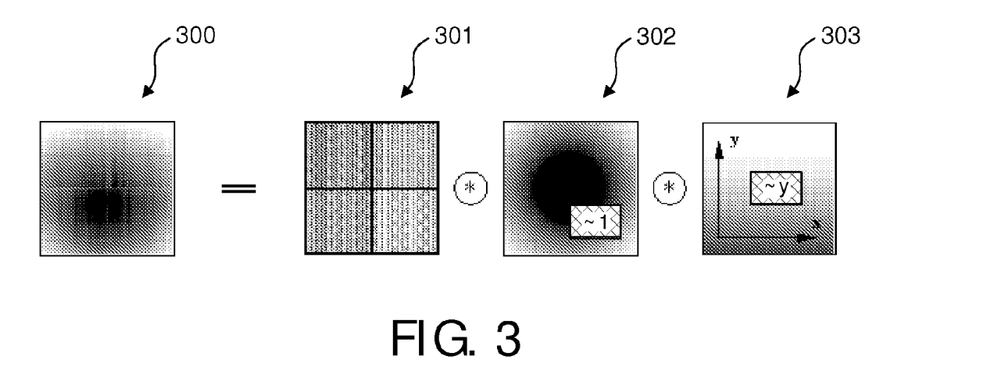
FIG. 3 to FIG. 5 illustrate different contributions to gain correction and corresponding artefacts.

FIG. 3 shows a resulting gain pattern 300 resulting from the combination of the detector gain contribution $G_{detector}$ 301, the $r^2$ term contribution $G_{radius}$ 302 and the heel effect term $G_{heel}$ 303.

According to an exemplary embodiment of the invention, only the term $G_{detector}$ or the product $G_{detector} \cdot G_{radius}$ is used for correction or calculating calibration parameters, but not $G_{heel}$.

Within such a procedure, no heel effect correction is performed. However, at first a fit function that models $G_{all}$ is defined. An appropriate selection is:

$$f(x,y)=ay^6+by^5+cy^4+dx^3+ey^3+fx^2+gy^2+hx+iy+j$$

The terms $G_{radius}$ and $G_{heel}$ can be derived from a fit to the $G_{all}$ data:

$$G_{radius}:r(x,y)=r_1(x^2+y^2)+r_2\sqrt{x^2+y^2}+r_3 \text{ with coefficients } r_1, r_2, r_3$$

$$G_{heel}:h(y)=h_1y^5+h_2y^4+h_3y^3+h_4y^2+h_5y+h_6.$$

It is mathematical equivalent to reintroduce the original heel effect after the regular gain correction $$\left(\text{Gain multiplicator}= \frac{1}{G_{all}} \cdot \frac{G_{heel}}{1}\right)$$

or to correct only for detector and radius specific terms $$\left(\text{Gain multiplicator}= \frac{1}{G_{detector} \cdot G_{radius}}\right).$$

The true heel effect is shown in a scheme 500 of FIG. 5.

The example image in FIG. 5 shows only the original heel effect from the right to the left. The vertical one is no more present. In this example, the radius dependent term is still corrected. There is another option to skip this correction as well, with the result that only the detector dependent term will be corrected. This would lead to a similar correction concept as for CR image plates, which may show the unmodified X-ray profile as well.

Figure 6:
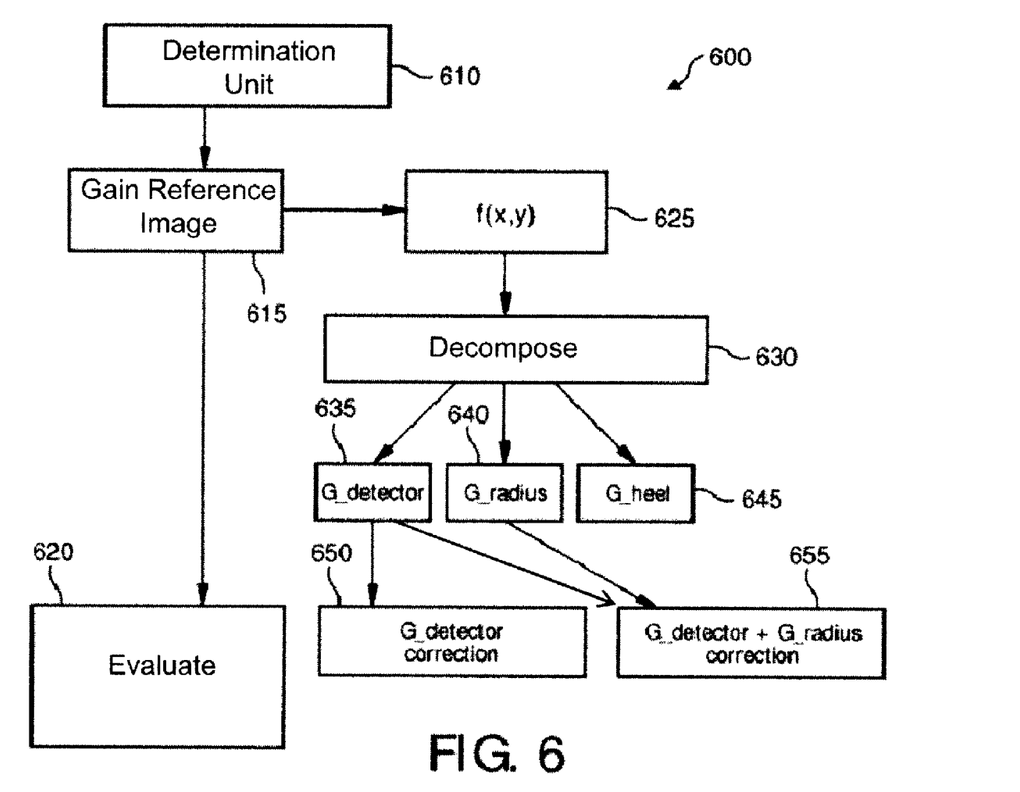
FIG. 6 shows a block diagram of a method of calibrating an X-ray image apparatus according to an exemplary embodiment of the invention.

In the following, referring to FIG. 6, a block diagram 600 illustrating a calibration method according to an exemplary embodiment of the invention will be explained.

In such a gain calibration scheme 610, a gain reference image 615 is captured. This gain reference image 615 may then be evaluated in a conventional manner, as indicated by a block 620, namely by considering $G_{detector}$, $G_{radius}$ and $G_{heel}$. However, alternatively, an embodiment of the invention allows to perform a fit using a model function f(x, y), as indicated by a block 625. A result of this fit allows to decompose the spectrum into three components, as indicated in a block 630. This allows to distinguish between a detector contribution 635 $G_{detector}$, a radius contribution $G_{radius}$ 640 and a heel effect contribution $G_{heel}$ 645.

According to one option, a correction based on $G_{detector}$ only is performed, as indicated in a block 650. Alternatively, a correction taking into account $G_{detector}$ and $G_{radius}$ may be performed, as indicated in the block 655.

Figure 7:
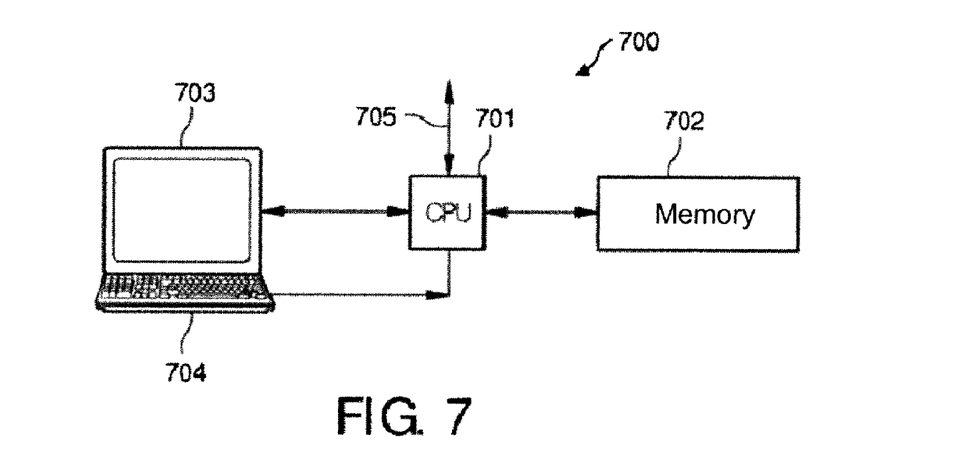
FIG. 7 shows an exemplary embodiment of a data processing device to be implemented in the system of the invention.

FIG. 7 depicts an exemplary embodiment of a data processing device 700 according to the present invention for executing an exemplary embodiment of a method in accordance with the present invention.

The data processing device 700 depicted in FIG. 7 comprises a central processing unit (CPU) or image processor 701 connected to a memory 702 for storing an image depicting an object of interest (such as a patient or an item of baggage) or a reference image. The data processor 701 may be connected to a plurality of input/output network or diagnosis devices, such as a CT device. The data processor 701 may furthermore be connected to a display device 703, for example a computer monitor, for displaying information or an image computed or adapted in the data processor 701. An operator or user may interact with the data processor 701 via a keyboard 704 and/or other output devices, which are not depicted in FIG. 7. Furthermore, via a bus system 705, it is also possible to connect the image processing and control processor 701 to, for example, a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the present invention may be applied advantageously, include baggage inspection, medical applications, material testing, and material science. An improved image quality and a reduced amount of calculations in combination with a low effort may be achieved. Also, the invention can be applied in the field of heart scanning to detect heart diseases.

It should be noted that the term "comprising" does not exclude other elements or features and the "a" or "an" does not exclude a plurality. Also elements described in association with different embodiments may be combined.

It should also be noted that reference signs in the claims shall not be construed as limiting the scope of the claims.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A calibration device for calibrating an X-ray image apparatus, the calibration device comprising:
   a receiving unit which receives an image captured by a detection unit of the X-ray image apparatus under reference conditions;
   an analyzing unit which analyzes the image captured under the reference conditions to derive gain correction information including gain correction due to a heel effect by performing a fit of a theoretical model to the image captured under the reference conditions;
   a calibration unit which provides the gain correction information without a gain correction due to the heel effect to the X-ray image apparatus for gain correcting images of examined objects.

2. The calibration device according to claim 1, wherein the reference conditions comprise capturing the image under essentially homogenous X-ray exposure conditions.

3. The calibration device according to claim 1, wherein the gain correction information derived by the analyzing unit includes a gain correction indicative of gain corrections due to a hardware characteristic of the detection unit, rotational artifacts, and the heel effect; and
   wherein the calibration unit provides gain correction information based on the gain correction due to the hardware characteristics and not the heel effect correction to the x-ray image apparatus.

4. A calibration device for calibrating an X-ray image apparatus, the calibration device comprising:
   a receiving unit which receives an image captured by a detection unit of the X-ray image apparatus under reference conditions;
   an analyzing unit which analyzes the image captured under the reference conditions to derive gain correction information by performing a fit of a theoretical model to the image captured under the reference conditions, the analyzing unit deriving the gain correction information from a gain correction due to a hardware characteristic of the detection unit and a gain correction due to rotational symmetric artifacts, and disregarding a gain correction due to a heel effect.

5. The calibration device according to claim 4, further including:
   a calibration unit which provides a calibration gain correction which is a mathematical function of the hardware characteristic gain correction and the rotational symmetric artifacts gain correction.

6. A calibration device for calibrating an X-ray image apparatus, the calibration device comprising:
   a receiving unit for receiving an image captured by a detection unit of the X-ray image apparatus under reference conditions;
   an analyzing unit for analyzing the image captured under the reference conditions to derive gain correction information;
   a calibration unit for providing calibrating information for calibrating the X-ray image apparatus based on the derived gain correction information and disregarding gain correction of a heel effect, the calibration unit being adapted for providing the calibrating information by calculating a gain correction factor by multiplying a gain correction factor indicative of gain correction due to a hardware characteristic of the detection unit with a gain correction factor indicative of rotational symmetric artifacts.

7. An X-ray image apparatus which examines an object of interest, the X-ray image apparatus comprising:
   an X-ray source which emits an X-ray beam to the object of interest;
   a detection unit which detects the X-ray beam having propagated through the object of interest to generate captured images;
   the calibration device according to claim 6, wherein the receiving unit receives the captured images from the detection unit and provides the calibrating information; and
   a determining unit which receives the calibrating information from the calibration unit and determines structural information concerning the object of interest based on the detected X-ray beam under consideration of the calibrating information.

8. The X-ray image apparatus according to claim 7, further comprising:
   a rotatable gantry, wherein the X-ray source and the detection unit are arranged on the gantry.

9. The X-ray image apparatus according to claim 7, wherein the apparatus includes:
   a computer tomography apparatus.

10. The X-ray image apparatus according to claim 7, configured as one of the group including a baggage inspection apparatus, a medical application apparatus, a material testing apparatus and a material science analysis apparatus.

11. The X-ray image apparatus according to claim 7, wherein the detection unit is movable.

12. The X-ray image apparatus according to claim 7, wherein the detection unit has two sides of different length.

13. A method of calibrating an X-ray image apparatus, the method comprising:
   receiving an image captured by a detection unit of the X-ray image apparatus under reference conditions;
   analyzing the image captured under the reference conditions to derive gain correction information including:
      determining gain correction information which corrects for image artifacts due to a heel effect;
   providing calibrating information for calibrating the X-ray image apparatus based on the derived gain correction information disregarding gain correction of the heel effect.

14. The method according to claim 13, wherein analyzing the image captured under reference conditions further includes:
   determining a hardware gain correction factor which corrects for image artifacts due to hardware characteristics of the detection unit; and
   determining a rotational symmetric artifacts gain correction factor which corrects for rotational symmetric image artifacts.

15. The method according to claim 14, wherein the calibrating information provided to the X-ray image apparatus includes a combination of the hardware gain correction factor and the rotational symmetric artifacts gain correction factor.

16. The method according to claim 15, wherein analyzing the image captured under reference conditions further includes:

fitting a polynomial model to the image captured under reference conditions.

17. The method according to claim 14, wherein the calibrating information provided to the X-ray image apparatus is a product of the hardware gain correction factor and the rotational symmetric artifacts gain correction factor.

18. A non-transitory computer-readable medium, in which a computer program of calibrating an X-ray image apparatus is stored which, when being executed by a processor controls or carries out the method of claim 13.

19. A program element of calibrating an X-ray image apparatus, which program element, when being executed by a processor and embedded in a non-transitory computer-readable medium, controls or carries out the method of claim 13.

* * * * *